United States Patent
Park et al.

(10) Patent No.: US 8,912,379 B2
(45) Date of Patent: Dec. 16, 2014

(54) METHOD OF PREPARING ALKENE COMPOUND

(75) Inventors: Dong-Kyung Park, Busan (KR); Chang-Heon Shon, Ulsan (KR); Duk-Suk Jung, Ulsan (KR); Young-Tae Song, Ulsan (KR)

(73) Assignee: Songwon Industrial Co., Ltd., Ulsan (KR)

( * ) Notice: Subject to any disclaimer, the term of this patent is extended or adjusted under 35 U.S.C. 154(b) by 0 days.

(21) Appl. No.: 13/580,715

(22) PCT Filed: May 31, 2010

(86) PCT No.: PCT/KR2010/003446
§ 371 (c)(1),
(2), (4) Date: Aug. 23, 2012

(87) PCT Pub. No.: WO2011/136432
PCT Pub. Date: Nov. 3, 2011

(65) Prior Publication Data
US 2013/0041197 A1    Feb. 14, 2013

(30) Foreign Application Priority Data
Apr. 26, 2010  (KR) .................. 10-2010-0038563

(51) Int. Cl.
*C07C 1/24*  (2006.01)
(52) U.S. Cl.
CPC ............... *C07C 1/24* (2013.01); *C07C 2527/19* (2013.01)
USPC .......................................... 585/639; 585/638

(58) Field of Classification Search
CPC .............. C07C 1/00; C07C 9/00; C07C 1/24; B01J 10/00; B01J 8/04
USPC .................................................. 585/638, 639
See application file for complete search history.

(56) References Cited

U.S. PATENT DOCUMENTS

| | | | | |
|---|---|---|---|---|
| 4,155,945 A | * | 5/1979 | Levine | 585/639 |
| 8,053,619 B2 | * | 11/2011 | Gracey | 585/640 |
| 2005/0014985 A1 | * | 1/2005 | Grund et al. | 585/639 |
| 2009/0118558 A1 | * | 5/2009 | Atkins et al. | 585/639 |
| 2009/0259086 A1 | * | 10/2009 | Bailey et al. | 585/639 |

FOREIGN PATENT DOCUMENTS

CN    101336216    12/2008
(Continued)

OTHER PUBLICATIONS

PCT/KR2010/003446 International Search Report and Written Opinion dated May 19, 2011, 67 pages.
(Continued)

*Primary Examiner* — In Suk Bullock
*Assistant Examiner* — Sharon Pregler
(74) *Attorney, Agent, or Firm* — Michael Best & Friedrich LLP

(57) ABSTRACT

Disclosed is a method of preparing an alkene compound including introducing an acidic catalyst and a solvent into a reactor, increasing a temperature the reactor, and continuously removing water from the reactor while continuously supplying an alcohol into the reactor and continuously collecting an alkene compound.

8 Claims, 1 Drawing Sheet

(56) References Cited

FOREIGN PATENT DOCUMENTS

| | | |
|---|---|---|
| CN | 101610835 | 12/2009 |
| DE | 3317165 | 11/1984 |
| EP | 0082937 | 7/1983 |
| EP | 0712824 | 5/1996 |
| EP | 1790627 | 5/2007 |
| EP | 1992601 | 11/2008 |
| JP | 54-135710 | 10/1979 |
| JP | 55-007213 | 1/1980 |
| JP | 55-009011 | 1/1980 |
| JP | 59-104376 | 6/1984 |
| JP | 59-210031 | 11/1984 |
| WO | 2008062157 | 5/2008 |

OTHER PUBLICATIONS

Chinese Office Action for the National Phase of PCT Application No. 201080065201X dated Nov. 26, 2013 (9 pages).

Invitation to Respond to Written Opinion for Singapore Patent Application No. 201206909-2 dated Oct. 14, 2013 (8 pages).

European Patent Office Extended Search Report for Application No. 10850798.9 dated Mar. 18, 2014 (6 pages).

Chinese Patent Office Action for Application No. 201080065201 dated Aug. 4, 2014 (9 pages, English translation included).

Japanese Patent Office Action for Application No. 2012-558057 dated Aug. 20, 2014 (3 pages).

\* cited by examiner

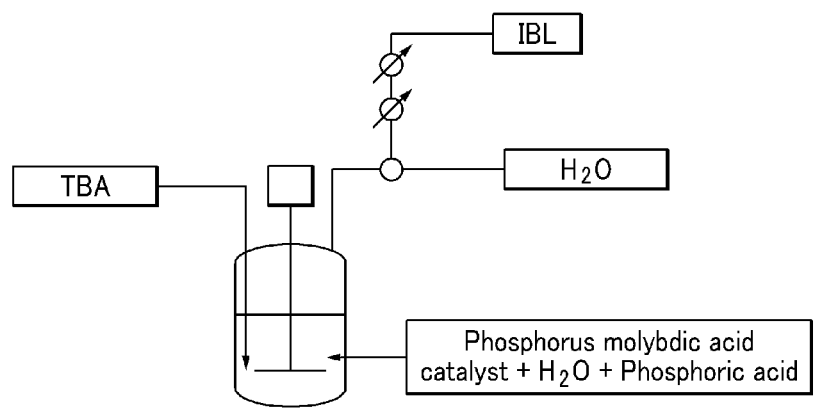

METHOD OF PREPARING ALKENE COMPOUND

CROSS-REFERENCE TO RELATED APPLICATIONS

This patent application is a national stage filing under 35 U.S.C. 371 of International Application No. PCT/KR2010/003446, filed 31 May 2010, which claims foreign priority to Korean Patent Application No. 10-2010-0038563, filed 26 Apr. 2010, the disclosures of which are incorporated by reference herein in their entireties. Priority to each application is hereby claimed.

TECHNICAL FIELD

This disclosure relates to a method of preparing an alkene compound.

BACKGROUND ART

A hydrocarbon mixture separated as a decomposition product from naphtha contains various kinds of hydrocarbon compounds.

Among them, 1,3-butadiene, isobutylene, and 1-butene are used as industrially applicable compounds. 1,3-butadiene is used as a raw material of synthetic rubber or plastic.

In addition, isobutylene is widely used to provide a butyl rubber, plastic stabilizers, a gasoline octane number improving agent, tertiary butanol, metacrylic acid, methacrylate ester, and the like. 1-butene may be used for a raw material of a plastic such as a polyolefin or the like.

The method of preparing an alkene compound, particularly isobutylene, includes cracking methyl tertiary butyl ether (MTBA) into isobutylene and methanol, or cracking t-butanol (TBA) into water and isobutylene.

In addition, the alkene compound may be prepared by a liquid homogeneous reaction using p-toluene sulfonic acid. The liquid homogeneous reaction includes: mixing a solvent such as benzene, toluene, xylene, or the like with p-toluene sulfonic acid in a reactor removing water from the mixture according to azeotropic distillation of the solvent and water to obtain a remaining reactant adding a t-butanol aqueous solution including about 15 to 40 wt % of water into a remaining reactant in the reactor; providing water and isobutylene according to the azeotropic distillation; and recycling the remaining solvent layer into the reactor. The obtained water and isobutylene are phase-separated to separate them.

However, since a lot of t-butanol is included in the removed water, there is a concern that the yield may be deteriorated. In addition, p-toluene sulfonic acid is strongly acidic, so a side reaction may occur. The liquid homogeneous reaction also causes problems of excessively using energy during the azeotropic distillation and of difficulty of providing isobutylene having excellent purity.

According to another method, isobutylene may be prepared from t-butanol or a t-butanol aqueous solution including at most 30 wt % of water under the conditions of a reaction temperature of 140 to 200° C., a pressure of 240 to 275 psig, and LHSV (liquid hourly space velocity) of 1 to 5 g/ml and using y-zeolite.

In this case, since the high temperature requires a high energy cost, in order to decrease the reaction temperature, a catalyst of silica-alumina is mixed with a diluent of alumina ceramic or active alumina, so as to further use the mixture as a catalyst. When the silica-alumina is further used, the reaction temperature may be decreased to 140 to 160° C., and the pressure may be decreased to the room pressure.

However, when the silica-alumina catalyst is further used, vapor or nitrogen gas may be further used as a diluting gas, so it may cause problems that the energy cost is increased to provide the diluting gas and to cool the diluting gas.

Furthermore, the method of using the strong acidic ion exchange resin is a method of preparing isobutylene by reacting a t-butanol aqueous solution having a concentration of 40 to 90 wt % with the strong acidic ion exchange resin using the strong acidic ion exchange resin under the conditions of 100 to 130° C., a pressure of 5 to 25 atm, and LHSV of 100 to 300. Thereby, the recycled amount is excessive compared to the raw material amount, so the yield is deteriorated. In addition, it may cause problems of high cost of maintaining the temperature of the recycled material and of transporting the same.

DISCLOSURE OF INVENTION

Technical Problem

One aspect of the present invention provides a method of preparing an alkene compound having an excellent yield.

Solution to Problem

According to one aspect of the present invention, a method of preparing an alkene compound is provided that includes introducing an acidic catalyst solution into a reactor, increasing a temperature of the reactor, and continuously removing water from the reactor while continuously supplying an alcohol into the reactor and continuously collecting an alkene compound.

Other aspects of the present invention are described in the following detailed description.

Advantageous Effects of Invention

The method of preparing an alkene compound according to the one embodiment may continuously provide an alkene compound in a high yield.

BRIEF DESCRIPTION OF DRAWINGS

FIG. 1 is a view showing a reactor according to one embodiment.

BEST MODE FOR CARRYING OUT THE INVENTION

Exemplary embodiments of the present invention will hereinafter be described in detail. However, these embodiments are only exemplary, and the present invention is not limited thereto.

The method of preparing an alkene compound according to one embodiment includes introducing an acidic catalyst and a solvent into a reactor, increasing a temperature of the reactor, and continuously removing water from the reactor while continuously supplying an alcohol into the reactor and continuously collecting an alkene compound. Hereinafter, the method according to one embodiment is described in detail.

First, an acidic catalyst and a solvent are introduced into a reactor. According to one embodiment of the present invention, the reactor may include any shape of reactor and is not specifically limited.

The acidic catalyst may be selected from the group consisting of a heteropoly acid, sulfuric acid, paratoluene sulfonic acid, and a combination thereof, and is preferably a heteropoly acid. The heteropoly acid is preferably since it is strongly acidic but is weakly corrosive to metal, so it may provide a coating layer on the surface of a metal to protect it. The heteropolyacid is an oxoacid having a main atom of tungsten and molybdenum, and includes phosphorus molybdic acid, phosphorous tungstic acid, silicon molybdic acid, silicon tungstic acid, phosphorus molybdenum tungstic acid, silicon tungsten molybdic acid, phosphorus vanadium tungstic acid, phosphorus vanadium molybdic acid, or a combination thereof.

The solvent may include water.

In addition, the acidic catalyst may be a solid-phase or a liquid-phase. When it includes the liquid acidic catalyst, it may be an aqueous solution. Whether the acidic catalyst is liquid or solid, the acidic catalyst may have a concentration of 10 to 80 wt %, preferably 20 to 80 wt %, and more preferably 40 to 70 wt % based on the total amount of the acidic catalyst and the solvent.

When the acidic catalyst has the ranged concentration, it may stably maintain the acidic catalyst and is economical.

Particularly, when the acidic catalyst is a heteropoly acid, the heteropoly acid has a concentration of 20 to 80 wt %, for example, 40 to 70 wt %.

Together with the acidic catalyst and the solvent, a phosphoric acid may be further added. When the phosphoric acid is further added, it may further increase the activity and stability of the acidic catalyst. When the phosphoric acid is further added, the phosphoric acid may be added at 0.1 to 3 parts by weight based on 100 parts by weight of the acidic catalyst. When the phosphoric acid is added within the range, it may effectively maintain the stability of the catalyst without causing problems of reactor corrosion.

Then the reactor is heated to increase a temperature of the reactor. The increasing a temperature process may be performed until the temperature of the reactor reaches 80 to 130° C., or for example 90 to 100° C.

The increasing temperature of the reactor to the temperature range may improve the reactivity, it may be economical, and further improves the yield.

Alcohol is continuously supplied into the reactor of which the temperature is increased. By supplying alcohol, an alkene compound and water are produced according to the decomposition reaction by the heteropoly acid catalyst. The produced water is continuously removed, and the resultant alkene compound is continuously collected to provide an alkene compound.

The produced alkene compound may be obtained as liquid or vapor depending upon the carbon number. When the produced alkene compound has a carbon number of 4 or less, it has a low boiling point at room pressure, so it is present as a vapor. On the other hand, when the produced alkene compound has a carbon number of 5 or more, it may be present as liquid at room pressure.

When a gas alkene compound is obtained, it may collect the same by capturing it.

The captured gas alkene compound may be liquefied by cooling or pressurizing conditions. The cooling condition may be performed at −10 to −15° C., and the pressurizing condition may be performed at a pressure condition of 0.5 to 8 kg/cm$^2$ by a compressor.

The obtained liquid resultant may be purified according to the general purifying process. For example, the purifying process may be performed by distillation under a pressure of 2 to 10 kg/cm$^2$.

In addition, the produced water may be obtained as a gas, but it may be removed by liquefying through a cooler since it has a boiling point of 100° C. As shown above, as much of the produced water may be removed as the introducing amount, so the concentration of the heteropoly acid may be constantly maintained in the reactor.

The alcohol may include a monohydric alcohol of R$^1$OH (R$^1$ is a C3 to C20 linear, branched, or ring alkyl group) or a dihydric alcohol of HO—R$^2$—OH (R$^2$ is a C4 to C20 linear, branched, or ring alkyl group). In addition, the alcohol may be an aqueous solution. When it is an aqueous solution, the alcohol concentration does not significantly affect preparation of the alkene compound, so it may be suitably adjusted.

The alcohol may be continuously supplied at a speed of 0.1 to 4.0 ml/minute based on 200 g of the acidic catalyst.

In addition, the water may be continuously removed at a speed of 0.1 to 2.0 ml/minute.

When the alcohol is continuously introduced at the ranged speed or the water is continuously at the ranged speed, it may enhance the conversion rate into the objective product of the alkene compound so improve the yield.

MODE FOR THE INVENTION

Hereinafter, the embodiments are illustrated in more detail with reference to examples. However, the following are exemplary embodiments and are not limiting.

COMPARATIVE EXAMPLE 1

100.0 g of a phosphorus molybdic acid catalyst aqueous solution having a concentration of 40 wt %, 2.0 g of phosphoric acid having a concentration of 85 wt %, 23.0 g of water, and 200.0 g of a t-butanol aqueous solution having a concentration of 87 wt % are introduced into a reactor and heated to increase a temperature to the temperature of 84.5° C. of the reactor. The phosphorus molybdic acid catalyst has a concentration of 24.6 wt % when the total weight of the phosphorus molybdic acid catalyst aqueous solution, the phosphoric acid, the water, and the t-butanol aqueous solution is considered as 100 wt %. Then it is reacted at the increased temperature for 330 minutes to provide and capture gaseous isobutylene. The phosphorus molybdic acid catalyst has a concentration of 24.6 wt % in the residue.

The obtained isobutylene gas is liquefied under the high pressure condition of 5 kg/cm$^2$ and distillated at a pressure of 4 kg/cm$^2$ and a temperature of 45° C. to provide purified isobutylene. The conversion rate of the isobutylene is 20 %.

COMPARATIVE EXAMPLE 2

100.0 g of a phosphorus molybdic acid catalyst aqueous solution having a concentration of 40 wt %, 2.0 g of phosphoric acid having a concentration of 85 wt %, 85.0 g of water, and 227.6 g of t-butanol are introduced into a reactor and heated to increase a temperature to the temperature of 82° C. of the reactor.

Then it is reacted at the increased temperature for 90 minutes to provide and capture gaseous isobutylene. The phosphorus molybdic acid catalyst has a concentration of 24.6 wt % in the residue.

The obtained isobutylene gas is liquefied under a high pressure condition of 5 kg/cm$^2$ and distillated at a pressure of 4 kg/cm$^2$ and a temperature of 45° C. to provide purified isobutylene. The conversion rate of isobutylene is 15%.

EXAMPLE 1

200 g of a phosphorus molybdic acid catalyst having a concentration of 40 wt %, 3.2 g of phosphoric acid having a concentration of 85 wt %, and 196.8 g of water are introduced into a round batch reactor shown in FIG. 1 and heated to increase a temperature to the temperature of 95° C. of the reactor.

At the increased temperature of 95° C., a t-butanol (TBA) aqueous solution having a concentration of 87 wt % is supplied into the reactant for 210 minutes at a speed of 0.7 ml/minute to provide a total of 102.3 g of t-butanol. The produced water is removed at a speed of 0.3 ml/minute, and the produced gas isobutylene is captured. The phosphorus molybdic acid catalyst has a concentration of 40 wt %.

The obtained isobutylene gas is liquefied under the high pressure condition of 5 kg/cm$^2$ and distillated at a pressure of 4 kg/cm$^2$ and a temperature of 45° C. to provide isobutylene (IBL). The conversion rate of isobutylene is 86.3%.

Then a t-butanol aqueous solution having a concentration of 87 wt % is supplied into the residue obtained after removing the water and isobutylene gas at a speed of 0.7 ml/minute to provide a total of 109.1 g of t-butanol.

Then it is reacted for 240 minutes while the reactor temperature is maintained at 94° C. The produced water is removed at a speed of 0.25 ml/minute, and the produced isobutylene is captured.

The obtained isobutylene gas is liquefied under the high pressure condition of 5 kg/cm$^2$ and distillated at a pressure of 4 kg/cm$^2$ and a temperature of 45° C. to provide purified isobutylene. The conversion rate of isobutylene is 87.9%.

EXAMPLE 2

A t-butanol aqueous solution having a concentration of 87 wt % is supplied into a reactor containing the residue remaining after removing water and isobutylene two times in Example 1 at a speed of 0.7 ml/minute to provide a total of 100.7 g of t-butanol. Then it is reacted for 140 minutes while the reactor temperature is maintained at 94° C. The produced water is removed at a speed of 0.2 ml/minute, and the produced isobutylene is captured.

The obtained isobutylene gas is liquefied under the high pressure condition of 5 kg/cm$^2$ and distillated at a pressure of 4 kg/cm$^2$ and a temperature of 45° C. to provide purified isobutylene. The conversion rate of isobutylene is 90.2%.

EXAMPLE 3

A t-butanol aqueous solution having a concentration of 87 wt % is supplied into a reactor containing the residue after removing water and isobutylene in Example 2 at a speed of 0.5 ml/minute to provide a total of 81.8 g of t-butanol. Then it is reacted for 230 minutes while the reactor temperature is maintained at 95° C. The produced water is removed at a speed of 0.15 ml/minute, and the produced isobutylene gas is captured.

The obtained isobutylene gas is liquefied under the high pressure condition of 5 kg/cm$^2$ and distillated at a pressure of 4 kg/cm$^2$ and a temperature of 45° C. to provide purified isobutylene. The conversion rate of isobutylene is 90.3%.

EXAMPLE 4

A t-butanol aqueous solution having a concentration of 87 wt % is supplied into a reactor containing the residue after removing water and isobutylene in Example 3 at a speed of 1.0 ml/minute to provide a total of 117.9 g of t-butanol. Then it is reacted for 170 minutes while the reactor temperature is maintained at 93° C. The produced water is removed at a speed of 0.3 ml/minute, and the produced isobutylene gas is captured.

The obtained isobutylene gas is liquefied under the high pressure condition of 5 kg/cm$^2$ and distillated at a pressure of 4 kg/cm$^2$ and a temperature of 45° C. to provide a purified isobutylene. The conversion rate of isobutylene is 89.4%.

EXAMPLE 6

200 g of a phosphorus molybdic acid catalyst having a concentration of 80 wt %, 3.2 g of phosphoric acid having a concentration of 85 wt %, 318.4 g of water are introduced into a batch reactor shown in FIG. 1 and heated to increase a temperature to the temperature of 94° C. of the reactor. The phosphorus molybdic acid catalyst has a concentration of 30.0 wt % in the entire reactant.

At the increased temperature of 94° C., a t-butanol aqueous solution having a concentration of 87 wt % is supplied into the reactant at a speed of 0.7 ml/minute to provide a total of 136.3 g of t-butanol. Then it is reacted for 277 minutes while the reactor temperature is maintained at 94° C. The produced water is removed at a speed of 0.2 ml/minute, and the produced isobutylene gas is captured. The phosphorus molybdic acid catalyst has a concentration of 30.0 wt % in the residue.

The obtained isobutylene gas is liquefied under the high pressure condition of 5 kg/cm$^2$ and distillated at a pressure of 4 kg/cm$^2$ and a temperature of 45° C. to provide purified isobutylene. The conversion rate of isobutylene is 87.9%.

EXAMPLE 7

A t-butanol aqueous solution having a concentration of 87 wt % is supplied into a reactor containing the residue after removing water and isobutylene in Example 6 at a speed of 0.5 ml/minute to provide a total of 83.2 g of t-butanol. Then it is reacted for 200 minutes while the reactor temperature is maintained at 95° C. The produced water is removed at a speed of 0.2 ml/minute, and the produced isobutylene gas is captured.

The obtained isobutylene gas is liquefied under the high pressure condition of 5 kg/cm$^2$ and distillated at a pressure of 4 kg/cm$^2$ and a temperature of 45° C. to provide purified isobutylene. The conversion rate of isobutylene is 89.4%.

EXAMPLE 8

A t-butanol aqueous solution having a concentration of 87 wt % is supplied into a reactor containing the residue after removing water and isobutylene in Example 7 at a speed of 1.0 ml/minute to provide a total of 126.8 g of t-butanol. Then it is reacted for 180 minutes while the reactor temperature is maintained at 93° C. The produced water is removed at a speed of 0.3 ml/minute, and the produced isobutylene gas is captured.

The obtained isobutylene gas is liquefied under the high pressure condition of 5 kg/cm$^2$ and distillated at a pressure of 4 kg/cm$^2$ and a temperature of 45° C. to provide purified isobutylene. The conversion rate of isobutylene is 86.0%.

EXAMPLE 9

A t-butanol aqueous solution having a concentration of 87 wt % is supplied into a reactor containing the residue after removing water and isobutylene in Example 8 at a speed of 0.3 ml/minute to provide a total of 81.8 g of t-butanol. Then it is reacted for 390 minutes while the reactor temperature is maintained at 97° C. The produced water is removed at a speed of 0.1 ml/minute, and the produced isobutylene gas is captured.

The obtained isobutylene gas is liquefied under the high pressure condition of 5 kg/cm$^2$ and distillated at a pressure of 4 kg/cm$^2$ and a temperature of 45° C. to provide purified isobutylene. The isobutylene has a conversion rate of 86.6%.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A method of preparing an alkene compound, comprising:
   introducing an acidic catalyst and a solvent into a reactor, wherein the acidic catalyst is present in a concentration of 10 to 80 wt %;
   heating the reactor to a temperature of 80 to 130° C.; and
   while continuously supplying an alcohol into the reactor at a speed of 0.1 to 4.0 ml/minute to produce the alkene compound and water, continuously removing the produced water from the reactor at a speed of 0.1 to 2.0 ml/minute, and continuously collecting the alkene compound.

2. The method of claim 1, wherein the acidic catalyst comprises an acidic catalyst selected from the group consisting of a heteropoly acid, sulfuric acid, paratoluene sulfonic acid, and a combination thereof.

3. The method of claim 2, wherein the acidic catalyst is a heteropoly acid.

4. The method of claim 1, wherein the acidic catalyst is present in a concentration of 20 to 80 wt %.

5. The method of claim 1, wherein the introducing an acidic catalyst and the solvent further comprises adding a phosphoric acid.

6. The method of claim 1, comprising heating the reactor to a temperature of 90 to 100° C.

7. The method of claim 1, wherein the alcohol is a monohydric alcohol of R$^1$OH (R$^1$ is a C3 to C20 linear or branched alkyl group) or a dihydric alcohol of HO—R$^2$—OH (R$^2$ is a C4 to C20 linear or branched alkyl group).

8. The method of claim 1, wherein the alcohol is t-butanol.

* * * * *